US00PP10640P

United States Patent [19]

Meyer

[11] Patent Number: Plant 10,640

[45] Date of Patent: Oct. 13, 1998

[54] CLIMBING ROSE PLANT NAMED 'WEKMEYER'

[75] Inventor: Lawrence E. Meyer, Hazelwood, Mo.

[73] Assignee: Weeks Wholesale Rose Grower, Inc., Upland, Calif.

[21] Appl. No.: 832,473

[22] Filed: Apr. 2, 1997

[51] Int. Cl.[6] ..... A01H 5/00

[52] U.S. Cl. ..... Plt./5

[58] Field of Search ..... Plt./5, 4, 2

[56] References Cited

U.S. PATENT DOCUMENTS

| | | | |
|---|---|---|---|
| P.P. 1,447 | 1/1956 | Boerner | Plt./2 |
| P.P. 1,459 | 3/1956 | Malandrone | Plt./5 |
| P.P. 2,386 | 3/1964 | Moore | Plt./5 |
| P.P. 3,682 | 2/1975 | Warriner | Plt./5 |

*Primary Examiner*—Howard J. Locker

*Attorney, Agent, or Firm*—Christie, Parker & Hale, LLP

[57] ABSTRACT

A new plant variety of climbing rose suitable for garden decoration, having flowers of light pink coloration.

1 Drawing Sheet

BACKGROUND OF THE INVENTION

This invention relates to a new and distinct variety of climbing rose. The varietal denomination of the new variety is 'Wekmeyer'. It was discovered as a naturally occurring branch mutation in a controlled planting of the cultivar 'Jacclam' (U.S. Plant Pat. No. 3,682).

SUMMARY OF THE INVENTION

The new variety is a bushy climbing plant, suitable for outdoor garden decoration. Among the features which distinguish the new variety from other presently available and known commercial rose cultivars are the following combination of characteristics: its very light pink flower coloration is unusual in climbing roses, its spicy fragrance, and its prolific bloom. 'Wekmeyer' may be asexually propagated by cuttings, budding or grafting.

Asexual reproduction of the new variety by budding as performed in Kern County and Upland, Calif., shows that the foregoing and other distinguishing characteristics come true to form and are established and transmitted through succeeding propagations.

Comparison with Parent

The new rose may be distinguished from its parent, 'Jacclam', by the following combination of characteristics: whereas 'Wekmeyer' produces flowers of a light pink coloration, 'Jacclam' produces flowers of a significantly darker coral pink coloration. However, the following characteristics of the parent are exhibited by the new variety:

Flower:

*Blooming habit.*—Recurrent, continuous; blooms on terminals of large canes and on laterals

*Bud.*—Size: ¾" to 1"long when petals start to unfurl. Form: Short, globular. Sepals: Color: Outer surface — mostly near Garnet Brown. Inner surface — Scheeles Green with white tomentum. Three appendaged sepals normally appendaged. Two unappendaged sepals hairy edged. Receptacle: Color: Green, overlaid in irregular areas with Garnet Brown. Shape: Funnel. Size: Large. Surface: Smooth. Peduncle: Length: Short. Surface: Slightly prickly. Color: Same as receptacle. Strength: Stiff, erect. Opening: Petals fold outwardly with a slight curling back of petal tips.

*Bloom.*—Size: Large; average size when fully expanded, 3 ½" to 4". Borne: Singly, and in flat clusters. Stems: Short. Form: When first open, flat. Permanence: Retains its form to the end. Petalage: Number of petals under normal conditions 40–45.

*Petals.*—Texture: Thick. Surface: Satiny. Shape: Deltoid with rounded outer edge. Form: Tips slightly recurved. Arrangement: Imbricated. Petaloids in center: Few. Persistence: Drop off cleanly. Lastingness: On the plant: Long. As cut flowers: Fair.

*Reproductive organs.*—Stamens, anthers: Medium. Color: Yellow. Arrangement: Regular around styles. Stamens, filaments: Long and short. Color Yellow. Pollen: Golden yellow. Stigmas: Color: Light yellow. Ovaries: All enclosed in calyx. Fruit: (Not observed).

Plant:

*Form.*—Climber.

*Growth.*—Very vigorous.

*Foliage.*—Size: Very large. Quantity: Abundant. Color: New Foliage: Much darker than Garnet Brown. Old foliage: Parsley Green.

*Leaflets.*—Shape: Oval pointed. Texture: Upper side: Leathery. Underside: Smooth. Ribs and veins: Ordinary. Edge: Serrated. Serration: Single. Petiole (rachis): Color: Upper edges: Garnet Brown. Lower edges: Green. Underside: Prickles. Stipules: Long, serrated. Disease resistance: Very resistant to mildew, rust and blackspot. Wood: New wood: Color: Light green, heavily covered wth Garnet Brown. Bark: Smooth. Old wood: Color: Green. Bark: Smooth. Thorns: Quantity: On main stalks from base — ordinary. On laterals from stalk — ordinary. Form: Broad base, hooked downwardly. Color: Red. Position: Irregular. Prickles: Quantity: On main stalks none; on laterals none. Short needles: Quantity: On main stalks none; on laterals none.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of this character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of October. Phenotypic expression may vary with environmental, cultural and climatic conditions, as well as differences in conditions of light and soil. The following description is directed primarily to the description of characteristics of the new variety that are different than the parent. In respect of characteristics not disclosed, the description is substantially the same as the parent, as described in U.S. Plant Pat. No. 3,682, the description in which is hereby expressly incorporated herein by reference.

Bud

The color of the under surfaces of the newly opened petals is between 49B and 36C. At the point where the petal attaches, there is a large zone of between 4C and 4D that slowly suffuses into the pink petal coloration. The color of the upper surfaces of the newly opened petals is between 49A and 36C. At the point where the petal attaches, there is a zone of near 4D that slowly suffuses into the predominant pink petal coloration.

Newly Opened Flower

The under surface of the outer petals is between 49C and 36C. At the point where the petal attaches, there is a large zone of between 4D and 10D that slowly suffuses into the pink petal coloration. The upper surface of the outer petals is between 49B and 36C. At the point where the petal attaches, there is a zone of near 4C that slowly suffuses into the pink petal coloration.

The under surface of the intermediate and inner petals is between 49C and 36C. At the point where the petal attaches, there is a large zone of between 4D and 10D that slowly suffuses into the pink petal coloration. The upper surface of the intermediate and inner petals is between 49A and 36C. At the point where the petal attaches, there is a zone of near 4C that slowly suffuses into the pink petal coloration.

The general tonality of the newly opened flower is between 49B and 36C.

Three Day Old Flower

The under and upper surface of the outer and inner petals is between 49D and 36D. At the point where the petal attaches on both the under and upper side, there is a large zone of near 155A that slowly suffuses into the pink petal coloration.

The general tonality of the three day old flower is between 49D and 36D.

In all other respects, the new variety substantially resembles its parent.

I claim:

1. A new and distinct variety of climbing rose plant, substantially as described and illustrated herein.

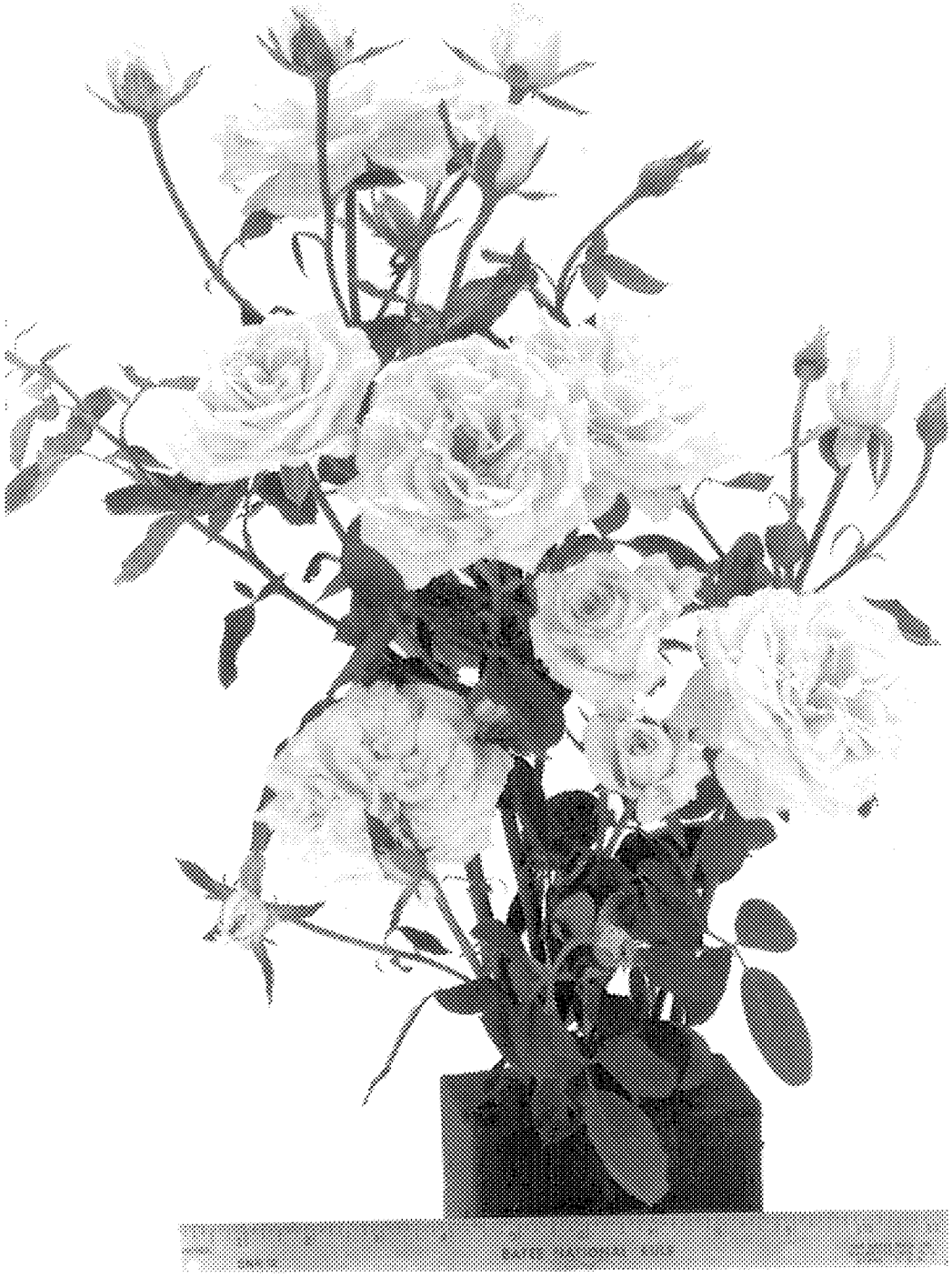

* * * * *